United States Patent [19]
Studier et al.

[11] Patent Number: 5,693,489
[45] Date of Patent: Dec. 2, 1997

[54] CLONING AND EXPRESSION OF THE GENE FOR BACTERIOPHAGE T7 RNA POLYMERASE

[75] Inventors: F. William Studier, Stony Brook, N.Y.; Parichehre Davanloo, Basel, Switzerland; Alan H. Rosenberg, Setauket, N.Y.; Barbara A. Moffatt, Waterloo, Canada; John J. Dunn, Bellport, N.Y.

[73] Assignee: Associated Universities, Inc., Washington, D.C.

[21] Appl. No.: 259,560

[22] Filed: Jun. 14, 1994

Related U.S. Application Data

[63] Continuation of Ser. No. 874,386, Apr. 27, 1992, abandoned, which is a continuation of Ser. No. 542,056, Jun. 22, 1990, abandoned, which is a continuation-in-part of Ser. No. 2,408, Dec. 29, 1986, Pat. No. 4,952,496, which is a continuation-in-part of Ser. No. 595,016, Mar. 30, 1984, abandoned.

[51] Int. Cl.$^6$ .................... C12N 15/67; C12N 15/00; C12N 15/70; C12N 1/21
[52] U.S. Cl. ............... 435/69.1; 435/172.3; 435/320.1; 435/252.33
[58] Field of Search ................. 435/91.3, 69.1, 435/172.1, 172.3, 320.1, 194, 252.33

[56] References Cited

FOREIGN PATENT DOCUMENTS 0178863  4/1986  European Pat. Off. .

OTHER PUBLICATIONS

Steen et al. (1986) EMBO J. vol. 5(5) pp. 1099–1105.
Tabor et al. (1985) PNAS vol. 82 pp. 1074–1078.
Mizusawa et al. (1982) Gene vol. 20 pp. 317–322.
Davauloo et al. (1984) PNAS vol. 81 pp. 2035–2039.
Mofflett et al., J. Mol. Biol., 173:265–269 (1984).
Studier et al., Dunn et al., J. Mol. Biol., 166: 477–535 (1983).
Studier et al., Cold Spring Harbor Symp. Quant. Biol., 47:999–1007 (1983).

*Primary Examiner*—Nancy T. Vogel
*Attorney, Agent, or Firm*—Margaret C. Bogosian

[57] ABSTRACT

This application describes a means to clone a functional gene for bacteriophage T7 RNA polymerase. Active T7 RNA polymerase is produced from the cloned gene, and a plasmid has been constructed that can produce the active enzyme in large amounts. T7 RNA polymerase transcribes DNA very efficiently and is highly selective for a relatively long promoter sequence. This enzyme is useful for synthesizing large amounts of RNA in vivo or in vitro, and is capable of producing a single RNA selectively from a complex mixture of DNAs. The procedure used to obtain a clone of the R7 RNA polymerase gene can be applied to other T7-like phages to obtain clones that produce RNA polymerases having different promoter specificities, different bacterial hosts, or other desirable properties. T7 RNA polymerase is also used in a system for selective, high-level synthesis of RNAs and proteins in suitable host cells.

1 Claim, 6 Drawing Sheets

CLONING AND EXPRESSION OF THE GENE FOR BACTERIOPHAGE T7 RNA POLYMERASE

CROSS REFERENCE TO RELATED APPLICATIONS

This application is a continuation of application Ser. No. 874,386 filed Apr. 27, 1992, and now abandoned, which is a continuation of application Ser. No. 542,056 filed Jun. 22, 1990, and now abandoned, which is a continuation-in-part of application Ser. No. 002,408 filed Dec. 29, 1986, now U.S. Pat. No. 4,952,496 issued Aug. 28, 1990, which in turn is a continuation-in-part of application Ser. No. 595,016 filed Mar. 30, 1984, and now abandoned.

This invention was made with Government support under contract number DE-AC02-76CH00016, between the U.S. Department of Energy and Associated Universities, Inc. The Government has certain rights in the invention.

BACKGROUND OF THE INVENTION

Bacteriophage T7 is a virulent bacteriophage that infects *Escherichia coli*. It belongs to a class of bacteriophages that specify relatively simple RNA polymerases that selectively transcribe the DNA of their own bacteriophage but do not transcribe unrelated DNAs [Hausmann, *Current Topics in Microbiology and Immunology*, 75, 77–110 (1976); Korsten, et al., *J. Gen. Virol.*, 43, 57–73 (1979); Towle, et at., *J. Biol. Chem.*, 250, 1723–1733 (1975); Butler and Chamberlin, *J. Biol. Chem.*, 257, 5772–5778 (1982); Chamberlin, et at., *Nature*, 228, 227–231 (1970); Dunn, et al., *Nature New Biology*, 230, 94–96 (1971)]. The T7 bacteriophage has been the subject of extensive scientific inquiry, in part because of its simple yet highly specific RNA polymerase. The genetic organization of T7 and the pattern of gene expression during infection are well understood, and the entire nucleotide sequence of T7 DNA is known (Studier and Dunn, *Cold Spring Harbor Symp. Quant. Biol.*, 47, 999–1007 (1983); Dunn and Studier, *J. Mol. Biol.*, 166, 477–535 (1983); Moffatt, et al., *J. Mol. Biol.*, 173, 265–269 (1984)]. These papers review and provide further references to a considerable body of work on T7 RNA polymerase.

T7 RNA polymerase, the product of T7 gene 1, is a protein produced early in T7 infection; it is a single-chain enzyme with a molecular weight close to 100,000. It appears that the basis for the selectivity of the T7 RNA polymerase is the interaction of the RNA polymerase with a relatively large promoter sequence, a sequence large enough that it is unlikely to be found by chance in any unrelated DNA. In the case of T7, the highly conserved promoter sequence appears to consist of approximately 23 continuous base pairs, which includes the start site for the RNA chain. If exact specification of even as few as 15 of these base pairs were required for initiation of chains, chance occurrence of a functional promoter would be expected less than once in a billion nucleotides of DNA.

The stringent specificity of T7-like RNA polymerases for their own promoter sequences is used by these phages to direct all transcription and replication to their own DNAs during infection. After the phage RNA polymerase is made, other phage gene products inactivate the host RNA polymerase, leaving all transcription in the cell directed by the phage enzyme.

T7 RNA polymerase is very efficient at transcribing DNA from its own promoters, and elongates RNA chains about five times faster than does *E. coli* RNA polymerase [Golomb and Chamberlin, *J. Biol. Chem.*, 249, 2858–2863 (1974)].

Termination signals for T7 RNA polymerase do not seem to occur very frequently, and termination is usually not very efficient [McAllister, et al., *J. Mol. Biol.*, 153, 527–544 (1981)].

Their selectivity, activity, and ability to produce complete transcripts make T7 RNA polymerase and the equivalent RNA polymerases from T7-like phages useful for a variety of purposes. T7 RNA polymerase and SP6 RNA polymerase have been purified from infected cells and have been used to produce RNAs for translation in vitro [Dunn and Studier, *J. Mol. Biol.*, 166, 477–535 (1983)], substrates for splicing [Green, et al., *Cell*, 32, 681–694 (1983)], and hybridization probes [Zinn, et al., *Cell*, 34, 865–879 (1983)]. T7 RNA polymerase made during T7 infection directs the expression of genes under control of T7 promoters in plasmids [Campbell, et al., *PNAS, USA*, 75:2276–2280 (1978); Studier and Rosenberg, *J. Mol. Biol.*, 153:503–525 (1981); and McAllister, et al., *J. Mol. Biol.*, 153:527–544 (1981)], but these gene products do not accumulate to high levels because of competition from promoters in T7 DNA and because the T7 infection quickly kills the cell. It was anticipated [McAllister, et al., *J. Mol. Biol.*, 153:527–544 (1981)], and the present invention demonstrates, that T7 RNA polymerase would also be useful for directing high-level expression of selected genes in cells. The problem in designing a high-level expression system is how to deliver active T7 RNA polymerase to a cell that contains a T7 promoter.

In the past, phage RNA polymerases like T7 RNA polymerase could be obtained only by infection with the phage from which they derive. The yield of purified RNA polymerase from infected cells is not particularly good, because the enzyme is synthesized for only a few minutes during the infection and does not accumulate to high levels. Nor is infection by these phages an efficient way to direct the transcription of non-phage genes inside the cell, because there is competition from promoters in the phage DNA itself and because the cells lyse within a short time.

Production of active T7 RNA polymerase from the cloned gene is an obvious way to obtain large amounts of enzyme for purification, and to haves a source of enzyme that could be introduced into a variety of cells without the disadvantages associated with infection by T7 itself. Presumably recognizing this, other workers attempted to clone the active gene from T7 DNA but were not successful. In one report, Stahl and Zinn [*J. Mol. Biol.*, 148:481–485 (1981)] obtained a clone of the entire gene except for the last nucleotide of the termination codon. However, loss of the termination codon causes additional amino acids to be added to the carboxy terminus, and the protein produced from the clone was inactive.

The present invention discloses a successful process for cloning and expressing the T7 RNA polymerase gene, a process that can also be applied to clone the RNA polymerase genes from other T7-like phages. The same method has subsequently been applied by Tabor and Richardson, *PNAS, USA*, 82:1074–1078 (1985) to obtain a different clone of the T7 RNA polymerase gene, and by Morris, et al., *Gene*, 41:193–200 (1986) to obtain a clone of the T3 RNA polymerase gene. Having a clone of the active gene enables the use of it for making large amounts of RNA polymerase for purification, and also enables the use of it to direct sustained, high-level expression of selected genes in the cells. The present invention discloses successful methods for implementing these uses of the cloned gene for T7 RNA polymerase in *E. coli*.

UTILITY STATEMENT

The ability of T7 RNA polymerase and equivalent RNA polymerases from T7-like phages to transcribe selectively any DNA that is linked to an appropriate promoter can serve as the basis for a very specific and efficient production of desired RNAs both in vitro and inside a cell. RNAs produced in vitro can be useful as hybridization probes (for specific medical diagnosis, for example), as mRNAs for in vitro protein synthesis, as substrates for analyzing processing reactions or RNA splicing, or for any purpose requiring a specific RNA. RNAs produced inside the cell can direct the production of specific proteins of interest (antigens for vaccines, hormones, enzymes, or other proteins of medical or commercial value, for example), can form complexes with specific mRNAs to inhibit their translation selectively, in vitro or in the cell, or can be useful for any purpose requiring a specific RNA. Potentially, the selectivity and efficiency of the phage RNA polymerase could make such production very efficient. Furthermore, the unique properties of these phage RNA polymerases may make it possible for them to direct efficient expression of genes that are expressed only inefficiently or not at all by other RNA polymerases- These phage polymerases have the further advantage that it is possible to selectively inhibit the host cell RNA polymerase so that all transcription in the cell will be due to the phage RNA polymerase.

This invention discloses the first means of cloning the active gene for T7 RNA polymerase, a process that can also be used to clone the RNA polymerases of other T7-like phages. It also discloses a process whereby large amounts of T7 RNA polymerase can be expressed and purified, and processes whereby T7 RNA polymerase from the cloned gene, and potentially the RNA polymerases of any of the T7-like phages, can direct the production of large amounts of RNAs and proteins in cells.

DEPOSIT

Three plasmids of this invention have been deposited in the American Type Culture Collection prior to the filing date of this application and in accordance with the permanency and accessibility requirements of the U.S. Patent and Trademark Office. Plasmid pAR1151 has ATCC No. 39561; pAR1173 has ATCC No. 39562; and pAR1219 has ATCC No. 39563.

Figure 6:
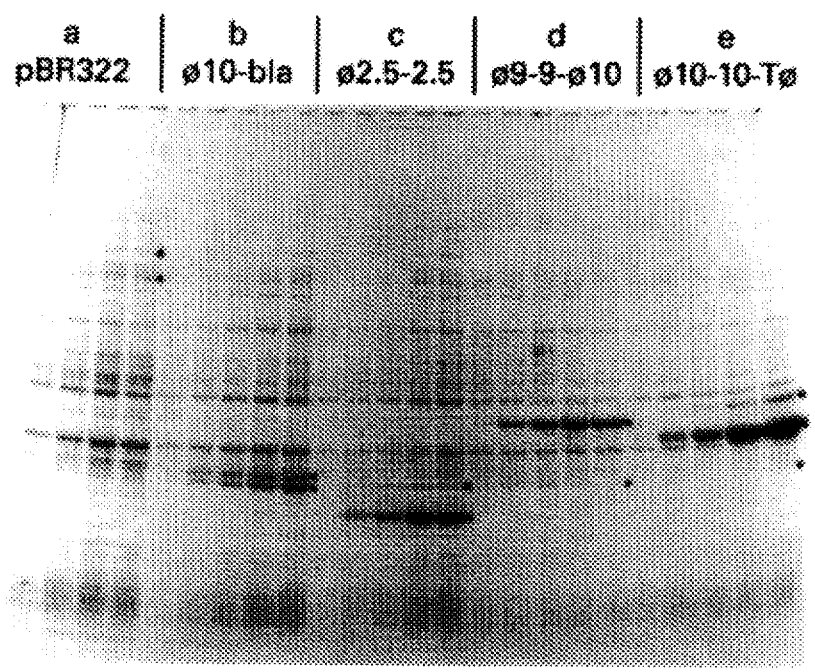

FIG. 6. Accumulation of protein directed by T7 RNA polymerase. Cultures of BL21(DE3) carrying the indicated plasmids were grown in ZY medium containing 200 μg ampicillin/ml, and synthesis of T7 RNA polymerase was induced by adding 0.4 mM-IPTG. The titer of samples of culture removed before IPTG was added showed that almost all of the cells had plasmid in each culture except that containing pAR511 (set (c)), where only about 87% of the cells had plasmid. Cells were collected by centrifugation, an amount equivalent to 10 l of culture was subjected to gel electrophoresis, and the proteins were visualized by staining with Coomassie brilliant blue. From left to right in each set, lanes represent samples collected immediately before, and 0.5, 1, 2 and 3 h after IPTG was added to the culture. The plasmids were: (a) pBR322, (b) pAR951, (c) pAR511, (d) pAR441 and (e) pAR436. Genes under control of T7 promoters in the plasmid are indicated above each set, as described in the legend to FIG. 2. The positions of β-galactosidase (higher) and T7 RNA polymerase (lower), whose synthesis is induced by IPTG, are marked by does in set (a). The positions of the proteins expressed from the plasmid under control of T7 promoters are marked in the other sets, including β-lactamase in sets (b) to (e) and both the gene 10A and 10B proteins in set (e).

Figure 7:
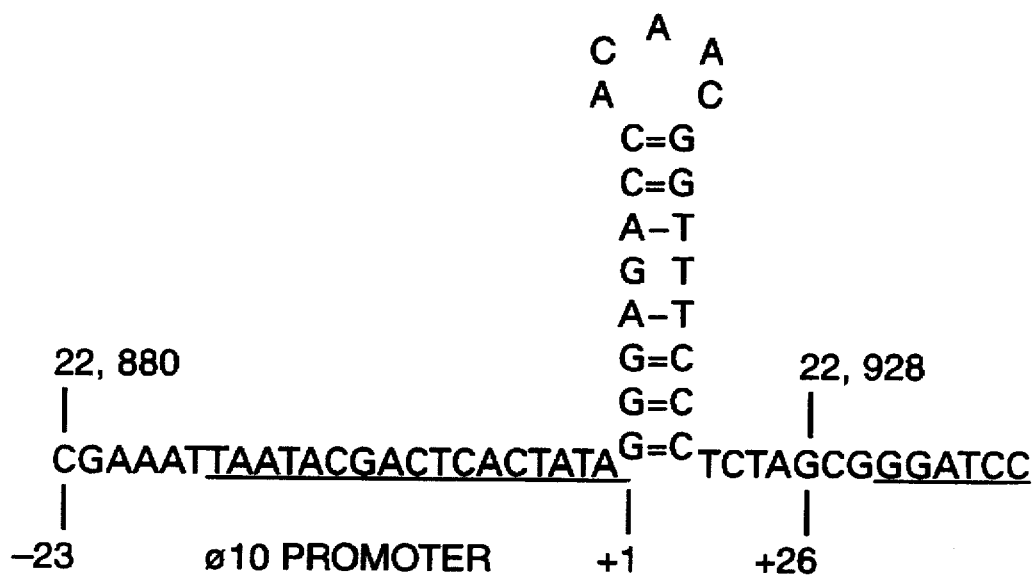

FIG. 7. Nucleotide sequence of the cloned φ10 promoter (−23 to +26), showing positions of the upstream conserved sequence of the φ10 promoter, the RNA start, a potential stem-and-loop structure in the RNA, and the downstream BamHI cloning site.

Figure 8:
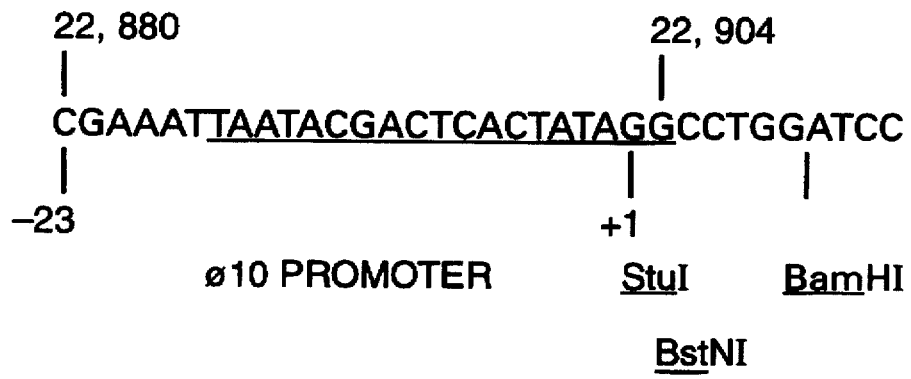

FIG. 8. Nucleotide sequence of the cloned φ10 promoter (−23 to +2), showing the conserved promoter sequence and the downstream linking sequence containing StuI, BstNI, and BamHI sites.

Figures 9, 10:

FIG. 9. Nucleotide sequence from the beginning of the cloned fragment of T7 DNA to the initiation codon of gene 10, showing positions of the φ10 promoter, the RNA start, a potential stem-and-loop structure in the RNA, a unique XbaI site, and the Shine-Dalgarno sequence.

FIG. 10. Nucleotide and amino acid sequences at the beginning of the gene 10 protein in the plasmids used for expressing coding sequences directly from the initiation codon or as fusions to the gene 10 protein.

DETAILED DESCRIPTION OF THE INVENTION

T7 RNA polymerase is active and efficient, is selective for its own promoters, and will make complete transcripts of almost any DNA that is linked to a T7 promoter. These properties make the enzyme very useful, but in combination they are also responsible for the failure of previous workers to clone the active T7 RNA polymerase gene. We recognized that a specific promoter for T7 RNA polymerase lies just past the end of the coding sequence, and we reasoned that it might be difficult or impossible to clone a DNA fragment that contained both an active polymerase gene and an active promoter. If such a fragment were cloned in a circular plasmid, for example, the polymerase would be able, by initiating at the promoter and transcribing around the plasmid, to direct the synthesis of its own mRNA. This would lead to an autocatalytic increase both in the level of T7 RNA polymerase and in the rate of transcription of the plasmid, which almost certainly would be lethal to the cell. Potentially, a single molecule of active T7 RNA polymerase would be sufficient to trigger this response, so such a construction would be stable only if there were absolutely no expression of the cloned gene by the host RNA polymerase, a situation that is difficult or impossible to achieve.

Cloning of genes in general does not have to contend with the problem of a gene product that can act on one or more sequences that might also be cloned along with the gene, and perhaps that is why previous workers were unable to clone the active T7 RNA polymerase gene. The process we devised to circumvent this problem for the RNA polymerases of T7-like phages and to obtain a clone of the active RNA polymerase gene consists of three steps, which are illustrated in the case of T7 RNA polymerase:

1) Identify the coding sequence for the RNA polymerase in the phage DNA. This can be done by standard techniques, as has been demonstrated for T7 RNA polymerase, and might include isolating and identifying amber mutations in the polymerase gene by their inability to make late RNAs or proteins [Studier, Science, 176:367–376 (1972)]; identifying the location of the gene in the phage DNA by testing for ability of mutants to recombine with cloned DNA fragments [Studier and Rosenberg, J. Mol. Biol., 153:503–525 (1981)]; and if necessary by determining the nucleotide sequence [Dunn and Studier, J. Mol. Biol., 166:477–535 (1983); Stahl and Zinn, J. Mol. Biol., 148:481–485 (1981)].

2) Identify the locations of the specific promoters for the phage RNA polymerase. Again in the case of T7, this has been done by transcribing the phage DNA or specific fragments of it with the phage RNA polymerase in vitro or in vivo [for example, Carter, et al., J. Virol., 37:636–642 (1981); McAllister, at al., J. Mol. Biol., 153:527–544 (1981)]. T7-like promoters typically have a conserved nucleotide sequence (23 continuous base pairs in the case of T7), and identification of this sequence would enable promoters to be identified in or near the nucleotide sequence of the RNA polymerase gene.

3) Isolate and clone a DNA fragment that contains the entire coding sequence for the RNA polymerase but no active promoter. The critical step in the entire process is to obtain a DNA fragment containing the coding sequence for an active RNA polymerase but no active promoters for the same RNA polymerase. It is also useful, but may not be in all cases necessary to remove any promoters for the RNA polymerase(s) of the host cell in which the clone will be propagated. The promoters can be removed or inactivated by standard techniques that are widely applied. A procedure we used is given in Example 1, but other commonly used procedures are equally applicable. For example, commonly used techniques for in vitro mutagenesis could be employed to introduce unique cleavage sites for restriction endonucleases at appropriate positions within cloned fragments containing the ends of the gene, the promoters could be removed by cleavage, and the intact gene without any promoters then reassembled from its separate fragments. In the unexpected event that a promoter for the phage RNA polymerase is located within the coding sequence for the RNA polymerase itself, this promoter would have to be inactivated by the now standard techniques of in vitro mutagenesis to eliminate promoter function without inactivating the gene. Once the nucleotide sequence of an RNA polymerase gene and its promoters is known, it would even be possible to synthesize a gene that will specify the correct amino acid sequence (or one that would make an active enzyme) but will not contain any active promoters.

The above process was used to clone the active gene for T7 RNA polymerase under conditions where its expression would be minimal, in case T7 RNA polymerase should be lethal. The BamHI site of the plasmid pBR322 was used as a cloning site because genes that are lethal if expressed to any significant extent had already been cloned in this site [Studier and Rosenberg, *J. Mol. Biol.*, 153, 503–525 (1981)]. To prevent expression of the cloned gene by the host RNA polymerase, a weak promoter for *E. coli* RNA polymerase that lies just ahead of the gene in the phage DNA was removed.

The above process will also provide active clones of the genes for similar RNA polymerases from other T7-like phages. T7-like phages are widely distributed in nature and infect many different types of bacteria. The genetic organization of all T7-like phages that have been examined has been found to be essentially the same as that of T7. Therefore, it is possible to isolate a DNA fragment containing the coding sequence for the RNA polymerase gene but not external promoters, in a way similar to that described for T7. Examples of T7-like phages include, but are not limited to *Escherichia coli* phages T3, φI, φII, W31, H, Y, A1, 122, cro, C21, C22, and C23; *Pseudomonas putida* phage gh-1; *Salmonella typhimurium* phage SP6; *Serratia marcescens* phage IV; Citrobacter phage VIIII; and Klebsiella phage No. 11 [Hausmann, *Current Topics in Microbiology and Immunology*, 75, 77–109 (1976); Korsten, et al., *J. Gen. Virol.*, 43, 57–73 (1975); Dunn, et al., *Nature New Biology*, 230, 94–96 (1971); Towle, et al., *J. Biol. Chem.*, 250, 1723–1733 (1975); Butler and Chamberlin, *J. Biol. Chem.*, 257, 5772–5778 (1982)]. The RNA polymerases of other T7-like phages have selectivities for their own promoters that are comparable to the selectivity of T7 RNA polymerase for its promoters, and several different, non-overlapping or partially overlapping promoter specificities are known. Clones of RNA polymerase genes from T7-like phages that are already known (or could be isolated from nature), together with their specific promoters, could be useful for directing the expression of specific genes in bacteria other than *E. coli*. Clones of RNA polymerases having non-overlapping specificities might also be useful for controlling two or more different sets of genes independently in a single cell. Certain T7-like RNA polymerases might also have properties such as temperature, pH, or ionic strength optima, kinetic properties, or stability that would make them particularly useful or desirable for particular applications.

By our preferred design, the clone of the gene for T7 RNA polymerase contains no promoter for *E. coli* RNA polymerase ahead of the gene. This makes it possible to control the expression of the gene by inserting appropriate promoters immediately ahead of it. To facilitate this process, we placed a unique cloning site ahead of the coding sequence so that any inserted promoter plus the coding sequence for T7 RNA polymerase can be removed as a single fragment for insertion into vectors suitable for different cell types (pAR1173, Example 3). In order to be able to make large amounts of T7 RNA polymerase for purification from *E. coli*, we inserted the inducible lacUV5 promoter for *E. coli* RNA polymerase at this site (pAR1219, Example 4). When this promoter is induced, T7 RNA polymerase accumulates to a level of perhaps 10–20% of the cell protein. This enzyme is soluble and active, and a simple purification procedure yields about 10–15 mg of pure protein from 100 ml of induced culture (Example 5 and 6). This is an ample and convenient supply of purified T7 RNA polymerase for most purposes. Of course, much larger amounts of T7 RNA polymerase could be obtained by starting with larger amounts of induced culture, or perhaps by placing a different promoter ahead of the cloned gene.

The cloned gene provides a source of active T7 RNA polymerase inside *E. coli* cells without the disadvantages inherent in T7 infection. Since T7 RNA polymerase is highly selective for its own promoters, which do not occur naturally in *E. coli*, the presence of a T7 promoter in the same cell should direct all transcription by T7 RNA polymerase in the cell to the DNA controlled by that promoter. Potentially, the entire resources of the cell could be directed to the production of selected RNAs and proteins.

In attempting to exploit the clone of gene 1 for this purpose, we initially attempted to place all of the elements needed for this expression system in a single plasmid. Starting with plasmid pAR1219, which contains gene 1 under control of the inducible lacUV5 promoter, we tried to add target genes under control of a T7 promoter. These efforts were unsuccessful, apparently because the basal levels of active T7 RNA polymerase in the uninduced state were such that the plasmids could not be maintained.

T7 RNA polymer see is so active and selective that we considered it might be difficult to find conditions where cloned gene 1 would be shut off to such a degree that the cell could tolerate diverse target genes, many of which might be toxic. To provide a completely general solution to this problem, we decided to remove gene 1 from the cell entirely, and to introduce it only at the time we wished it to be active. In this way, we separate the system into two parts:

1) the source of T7 RNA polymerase from the cloned gene, and
2) the target gene under control of a T7 promoter.

In the two-part configuration, target genes could be cloned in the host cell under control of a T7 promoter without enhancing their expression, since *E. coli* RNA polymer see (and presumably the RNA polymerases of almost any potential host cell) does not initiate transcription at T7 promoters. If target genes are cloned in sites where the host RNA polymer see makes little or no mRNA from them, even genes whose products are very toxic to the cell should be tolerated under control of a T7 promoter. The gene for T7 RNA polymerase could be placed in a virus, but under control of promoters for the host cell or vital RNA polymerase (if any). Upon infection with the virus, active T7 RNA polymer see would be produced and would in turn transcribe the target DNA that is under control of the T7 promoter.

A specific configuration for expression in which the target gene is cloned in the silent orientation in the BamHI site of pBR322 and the T7 RNA polymerase is delivered by a derivative of phage lambda is described in the examples. In this configuration, it is possible to direct essentially all of the resources of the cell to the production of target genes and proteins, and to accumulate large amounts of selected RNAs and proteins. This configuration was used to work out the properties of the T7 expression system, but it is not intended that the process be limited to this specific configuration. We expect that this process for gene expression will be successful with the target genes cloned in many different types of vectors or in the chromosome of the cell; with T7 RNA polymerase delivered by other types of virus besides lambda; with clones of other T7-like RNA polymer sees, alone or in combination, together with target genes controlled by their specific Promoters; and in other cell types besides *E. coli*, both prokaryotic and eukaryotic.

A complementary two-part configuration is also possible, in which the target gene is placed under control of a T7 promoter in the virus and the gene for T7 RNA polymerase is maintained in the cell under control of an inducible or constitutive promoter for the host RNA polymerase. In this configuration, it is possible to adjust the level of active T7 RNA polymerase present in the cell before delivery of the target gene by the virus. So far, the levels of expression produced in this configuration have not been as high as in the first process.

Although the properties of the T7 expression system were defined in the first configuration described above, it is also useful to be able to have a system where all parts are resident in the same cell. We have achieved such a unitary process as well. In this configuration a single copy of the gene for T7 RNA polymerase is placed in the chromosome of the cell under control of an inducible promoter for the host cell RNA polymerase and the target gene is placed under control of a T7 promoter in a multi-copy plasmid vector. With only a single copy of the T7 RNA polymerase gene in the cell, the basal activity in the uninduced state is low enough that many but not all target genes can be tolerated in the same cell. When the system is stable enough, the amounts of RNA and protein that can be produced are equally as large as in the first configuration above.

A specific unitary process for expression in which the target gene is cloned in the silent orientation in the BamHI site of pBR322 and the T7 RNA polymerase is placed in the chromosome as a lysogen of a derivative of phage lambda, and where the gene for T7 RNA polymerase is under control of the inducible lacUV5 promoter, is described in the examples. In this configuration, as in the first, it is possible to direct essentially all of the resources of the cell to the production of target genes and proteins, and to accumulate large amounts of selected RNAs and proteins. While this configuration is successful, it is not intended that the process be limited to this specific configuration. We expect that this process for gene expression will be successful with the T7 RNA polymerase gene cloned in the chromosome of the cell under control of many different inducible promoters; with the target genes cloned in many different types of single or multi-copy vectors or in the chromosome; with clones of other T7-like RNA polymerases, alone or in combination, together with target genes controlled by their specific promoters; and in other cell types besides *E. coli*, both prokaryotic and eukaryotic. In particular, since not much T7 RNA polymerase seems to be needed to produce very high levels of expression of target genes, inducible promoters that are very well shut off may be useful in allowing more toxic target genes to be tolerated even if the promoter is not very strong upon induction.

Conditions for optimal expression of target genes in *E. coli* were established using T7 genes under control of T7 promoters (examples 9–11). These examples show clearly that T7 RNA polymerase is capable of focusing the resources of the cell on the production of target proteins under control of a T7 promoter in a plasmid. The extent of the response depends upon the amount of T7 RNA polymerase present, but relatively small amounts generate a large response. The rate of synthesis of the target protein can be much higher than the rate of synthesis of any host protein, and such high rates can continue for three hours or longer. In any case, the large accumulation of RNA makes it seem likely that T7 RNA polymerase transcribing from a T7 promoter in a multicopy plasmid is capable of producing enough mRNA to saturate the protein-synthesizing machinery of *E. coli*.

Plasmid vectors have been constructed (examples 14 and 15) that allow DNA fragments from virtually any source to be placed under control of the strong $\phi 10$ promoter for T7 RNA polymerase, or under control of this promoter plus the protein initiation signals of T7 gene 10, the gene for the major capsid protein of T7. Some of these vectors also contain the transcription termination signal T$\phi$ from T7 DNA. The control sequences have been cloned so that they can easily be removed from these vectors and inserted in other plasmids, viruses or chromosomes to create a wide variety of other vectors and configurations for T7 RNA polymerase-directed expression of cloned DNA fragments both in vivo and in vitro. And of course, equivalent sets of vectors can also be created from the analagous control elements from other T7-like phages for use with their specific RNA polymerases.

The following examples provide additional elucidation of the plasmids and processes of this invention. Descriptions of the invention can also be found in Davanloo, et al., *PNAS, USA* 81:2035–2039 (1984) and in Studier and Moffatt, *J. Mol. Biol.*, 189:113–130 (1986). These examples are not intended to unduly restrict the invention to the uses described therein. In these examples, the following materials and methods were employed throughout:

1. *E. coli* HMS174 [as described in Campbell, et al., *Proc. Natl. Acad. Sci. USA*, 75, 2276–2280 (1978)] or BL21, a Met⁺ derivative of B834 [described by Wood, *J. Mol. Biol.*, 16:118–133 (1966)] were used as the host for plasmid strains.

2. Bacteriophage T7, suitable hosts, and techniques for growing and manipulating them were used as described in Studier, *J. Mol. Biol.*, 94,283–295 (1975); Studier, *J. Mol. Biol.*, 79, 227–236 (1973); and Studier, *Virology*, 39, 562–574 (1969). The nucleotide sequences, locations, and designations of T7 genes and genetic elements are given in Dunn & Studier, *J. Mol. Biol.* 166, 477–535 (1983) and Moffatt, et al., *J. Mol. Biol.* 173, 265–269 (1984).

3. DNA fragments were cloned in the plasmid pBR322, the plasmid described in Bolivar, et al., *Gene*, 2, 95–113 (1977).

4. The preparation and cloning of DNA fragments was by standard techniques as described in *Methods in Enzymology*, Volume 68, (1979), R. Wu, ed., Academic Press, New York, and *Molecular Cloning: A Laboratory Manual* (1982) by Maniatis, et al., Cold Spring Harbor Laboratory Press, Cold Spring Harbor, N.Y., and Studier and Rosenberg, *J. Mol. Biol.*, 153, 503–525 (1981).

5. The source of lacI-lacUV5 promoter DNA was the plasmid pMCI described in Calos, *Nature (London)*, 274, 762–765 (1978). Transcription from the lacUV5 promoter was induced by adding 0.4 mM isopropyl-beta-D-thiogalactoside (IPTG) to growing cultures.

6. Restriction endonucleases and enzymes used in cloning DNA were obtained from New England Biolabs, Bethesda Research Laboratories, or Boehringer Mannheim.

7. Synthetic deoxynucleotide linkers containing a BamHI site or a BglII site were obtained from New England Biolabs.

8. Preparation of the T7 Deletion Mutants. A number of deletions lying to the left or right of gene 1, the gene for T7 RNA polymerase, have been described and characterized [Studier, et al., *J. Mol. Biol.*, 135, 917–937 (1979)]. These deletions apparently arose by genetic crossovers between short repeated sequences. The crossover for D159 is at the sequence A-A-T-G-C-T-G-A, located at nucleotides 975 and 3023 in the nucleotide sequence of T7 DNA, and the crossover for C74 is at the sequence G-T-G-G-C-C-T, located at nucleotides 1458 and 3128 [Dunn and Studier, *J. Mol. Biol.*, 166, 477–535 (1983) and Studier, et al., *J. Mol. Biol.*, 135, 917–937 (1979)]. The likely crossover sequences for LG4 (A-A-T-A-C-G-A-C-T-C-A-C-T-A at 5832 and 7879) and LG26 (G-G-T-A-A-G-A-A at 7165 and 8658) were deduced from restriction mapping and the locations of repeated sequences in this region of T7 DNA. Heteroduplexes between the DNAs of double-deletion mutants D159,LG4 and C74,LG26, when digested with the single-strand-specific nuclease S1, would be expected to produce a fragment extending from nucleotides 3128 to 5845, which would contain the entire coding sequence for T7 RNA polymer see. The double-deletion strains were constructed by conventional genetic crosses, and the presence of both deletions in each double-deletion strain was confirmed by restriction analysis of the DNA.

9. Growth media. The practice of this invention includes, but is not limited to the following complex growth media: ZB medium (10 g N-Z-amine A/l and 5 g NaCl/l); ZY medium 10 g N-Z-amine A/l, 5 g Bacto yeast extract/l, and 5 g NaCl/l); or M9 medium (1 g $NH_4Cl/l$, 3 g $KH_2PO_4/l$, 6 g $Na_2HPO_4 4/l$, 4 g glucose/l, and 1 ml 1 m-$MgSO_4$/l); B2 medium (M9 medium in which all but 0.16 mM of the phosphate is replaced by salts and bis-Tris buffer); M9ZB medium (combines M9 and ZB media); M9 maltose and B2 maltose are the equivalent media, in which glucose is replaced by maltose. N-Z-amine A is commercially available from Sheffield Products; Bacto Tryptone and yeast extract are commercially available from Difco. When growing plasmid-containing cells, ampicillin was added to the medium, usually at a concentration of 20 ug/ml, but as high as 200 ug/ml. Dilutions of bacteria or phage for titering were made in ZB medium, and samples were plated by mixing with 2.5 ml of melted rop agar [0.7% (w/v) agar in ZB medium], and spreading on plates containing 20 ml of hardened bottom agar (1% agar in ZB medium).

10. Maniatis, et al., *Molecular Cloning: A Laboratory Manual*, Cold Spring Harbor Laboratory Press, Cold Spring Harbor, N.Y. (1982) discloses general procedures for working with lambda; the specific procedures followed for the present invention include: phage stocks were grown in ZY medium. Stock lysates were grown by adding a single plaque and 50 μl of a fresh overnight culture of ED8739 to 35 ml of growth medium in a 125 ml flask, and shaking at 37° C. until lysis; larger volumes were grown by adding 10 μl of lysate and 1 ml of cells to 500 ml of medium in a 1 liter flask. Lysates typically contained a few times $10^{10}$ infective phage particles/ml.

Phage were purified by precipitation with polyethylene glycol, followed by rapid isopycnic banding in CsCl step gradients. All solutions used during purification, including CsCl solutions, contained 10 mM-Tris Hcl (pH 8.0), 10 mM-$MgSO_4$, and 100 μg gelatin/ml to keep the phage intact. The purified phage were stored in the. CsCl solution, and dilutions were made in 0.1 M-NaCl, 50 mM-Tris Hcl (pH 8.0), 10 mM-$MgSO_4$, and 100 μg gelatin/ml.

11. Cloning vector D69, the cloning vector used in the production of target gene proteins, is a lambda derivative that has imm[21] and a single BamHI cloning site within the int gene. This vector is described in Mizusawa, et al., *Gene*, 20:317–322 (1982). A mixture of 500 ng of a BamHI digest of D69 DNA and a 5-fold molar excess of a BamHI fragment that contained the gene for T7 RNA polymerase (purified from pAR1151 or pAR1219) was ligated with phage T4 DNA ligase and packaged in a lambda packaging system. About 90% of the resulting plaques contained inserts (of both orientations). Cloning into the BamHI site of D69 interrupts the int gene, whose produce is needed for integration into the chromosome. Therefore, to form lysogens of the D69 derivatives that contain gene 1, int function was provided from a lysogen of heterologous immunity. A drop of lysate was spotted onto a lawn of the helper lysogen, the center of the cleared spot was used to grow a culture, and individual colonies from the culture were tested for the appropriate immunity or for the presence of a functional cloned gene. The genetic composition of D69 and the derivatives used in this process are shown in Table 1 and FIG. 1.

12. Rates of synthesis and accumulations of RNAs and proteins were analyzed by standard techniques of agarose and polyacrylamide gradient gel electrophoresis, as described in Studier, *J. Mol. Biol.*, 79:237–248 (1973 and *Molecular Cloning: A Laboratory Manual* (1982) by Maniatis, et al., Cold Spring Harbor Laboratory Press, Cold Spring Harbor, N.Y.

EXAMPLE 1

Isolation of Gene 1 Fragments Lacking T7 Promoters

Search of the nucleotide sequence revealed no restriction sites that would permit convenient isolation of a fragment containing the entire gene 1 coding sequence but not the *E. coli* promoter located ahead of the coding sequence or the T7 promoter immediately following it. Therefore, an appropriate fragment was isolated from heteroduplexes formed between the DNAs of different deletion mutants of T7. The procedure is similar to that employed by Stahl and Zinn, *J. Mol. Biol.*, 148, 481–485 (1981), except that heteroduplexes from overlapping double-deletion mutants were prepared in order to provide an optimal substrate for the single-strand specific endonuclease S1.

Following the techniques described in Studier, *J. Mol. Biol.*, 41, 199–209 (1969), heteroduplexes between the DNA of the double-deletion strains D159,LG4 and C74,LG26 were prepared directly from concentrated stocks of phage particles that had been purified by isopycnic banding in CsCl solution containing small amounts of Tris and EDTA. The stocks in CsCl solution were diluted 50 fold in 30 mM NaOH and left for 10 min. at room temperature to release and denature the DNA. The final DNA concentration was 100 μg/ml. The DNA mixture was neutralized by adding 0.1 volume of 0.5M Tris-Cl, pH 6.8, and the DNA was renatured by incubating 10 min. at 65° C. The renatured DNA was precipitated with ethanol and redissolved in 5 mM Tris-Cl, pH 6.8. The solution was adjusted to one-third the original volume and to a composition of 0.3M NaCl, 4.5 mM $ZnSO_4$, 30 mM sodium acetate, pH 4.6, for treatment with S1 nuclease. After digestion sufficient to release the double-stranded fragments from the heteroduplexes, the DNA mixture was subjected to electrophoresis on a 1% agarose gel, where the gene 1 fragment migrated as a sharp band well resolved from the other digestion products.

EXAMPLE 2

Construction of Plasmid pAR1151

Because of the possibility that a functional promoter for T7 RNA polymerase might remain in the fragment produced by S1 nuclease digestion of the heteroduplex DNA, we also digested the gene 1 fragments very lightly with BAL-31 exonuclease, to remove a few nucleotides from the ends of the fragment. The fragments generated by S1 alone, or by S1 followed by BAL-31 treatment, were purified by gel electrophoresis and adapted with BamHI linkers (CCGGATCCGG) for insertion into the BamHI site of pBR322. The ligation mixture was used to transform *E. coli* HMS174 to ampicillin resistance, and the transformants were enriched for tetracycline-sensitive clones by treatment with cycloserine.

When individual transformants from several different ligation mixtures were tested by gel electrophoresis of the plasmid DNAs, very few inserts were found, and none contained a complete gene 1. To enrich for plasmids containing an intact gene, plasmid DNA prepared from a mixed population of transformants obtained after cycloserine enrichment was subjected to gel electrophoresis, and DNA was recovered from the region of the gel where plasmids containing complete gene 1 would be expected to migrate. This DNA was then used to transform *E. coli* HMS174, and 48 new tetracylcine-sensitive clones were isolated and analyzed for inserts. Four of these 48 plasmid DNAs appeared to carry an insert of the proper size to contain all of gene 1. Gel electrophoresis of the fragments produced by cutting these plasmid DNAs with HindII and with KpnI produced identical patterns from all four clones, which were essentially the patterns expected if the entire gene had been cloned in the silent orientation. The fragments cloned in this experiment had been treated with BAL-31.

One of the plasmids produced by the above procedure which appeared to carry an insert of the proper size to contain all of gene 1 was pAR1151. To determine exactly where the cloned fragment begins and ends in the nucleotide sequence of T7 DNA, the fragment was released from the plasmid by cutting with BamHI and the nucleotide sequence at each end was determined by the techniques of Maxam and Gilbert (*Methods in Enzymolgy*, 65, 499–560, Academic Press, New York, 1979). The results showed that, after accounting for the sequence of the BamHI linkers, the fragment that was cloned in pAR1151 begins at nucleotide 3146 of T7 DNA and ends at nucleotide 5840. Because the last nucleotide of the linker at the left end of the fragment happens to be the same as nucleotide 3145 of T7 DNA and the first nucleotide of the linker at the right end the same as nucleotide 5841, the actual limits of T7 DNA sequence are 3145–5841, that is, position 7.88–14.63 in T7 DNA. Therefore, the cloned fragment contains slightly more than the entire coding sequence for T7 RNA polymerase.

Compared with the minimum fragment expected from S1 treatment of the heteroduplex DNA, the cloned fragment of pAR1151 has lost 19 base pairs from the left end and five from the right end, presumably because of the BAL-31 treatment. The first six nucleotides of the natural mRNA are missing, but the fragment does contain 26 base pairs ahead of the AUG initiation codon, and therefore has the entire predicted ribosome-binding and initiation region. The last 46 nucleotides of the natural mRNA are also missing, but the fragment contains 19 base pairs beyond the end of the coding sequence. The cloned fragment contains only the first 11 of the 23 highly conserved base pairs of the promoter for T7 RNA polymerase just past the end of the coding sequence and has no promoter activity for T7 RNA Polymerase.

The plasmid pAR1151 was tested to determine if it produced active T7 RNA polymerase. When a cloned fragment of T7 DNA can express a functional gene, T7 amber mutants defective in that gene are usually able to plate with high efficiency on a restrictive host that carries the cloned fragment. In the case of gene 1 amber mutants, active T7 RNA polymerase is absolutely required to produce any increase in plating efficiency above the reversion frequency. We expected that little if any active T7 RNA polymerase would be produced from pAR1151, because the cloned gene is in the silent orientation in the BamHI site of pBR322, where little gene 1 mRNA should be produced. However, we found that gene 1 amber mutants form plaques on HMS174/pAR1151 with the same efficiency as on a host that carries an amber suppressor, although the plaques are somewhat variable in size. Clearly, active T7 RNA polymerase can be made in these cells. The variability of plaque size suggests that the level of active enzyme in the cell may be rather low but high enough that plaques are eventually produced from virtually every infection.

EXAMPLE 3

Construction of Plasmid pAR1173

In order to make large amounts of T7 RNA polymerase from the cloned gene, it was necessary to increase the synthesis of the gene 1 mRNA. To facilitate construction of plasmids in which promoters could be placed ahead of gene 1, a derivative of pAR1151 was first made in which a BglII site was inserted into the BamHI site ahead of gene 1. There are no BglII sites in gene 1 or pBR322, so the inserted BglII site provides a unique cloning site immediately ahead of gene 1. The construction was made by partial digestion of pAR1151 with BamHI, filling in the ends with DNA polymerase, attaching synthetic BglII linkers (CAGATCTG), digesting with BglII, and religating the exposed BglII sites. Because of the sequence of the linkers, a BamHI site should be regenerated to each side of the BglII site. The modified plasmid selected, pAR1173, does not contain a BamHI site between the BglII site and gene 1, presumably due to some imperfection in the cutting and ligation reactions. This is a convenient result because sequences that are inserted in the BglII site will remain with gene 1 as a single fragment upon digestion with BamHI, allowing promoter-gene 1 constructs made in pAR1173 to be moved easily to other vectors.

EXAMPLE 4

Construction of Plasmid pAR1219 and Lambda Derivatives That Carry the T7 RNA Polymerase Gene One promoter that has been inserted into the BglII site ahead of gene 1 in pAR1173 is the inducible lacUV5 promoter, which remains sensitive to the lac repressor but is no longer subject to catabolite repression [Silverstone, et al., *PNAS*, 66:773–779 (1970)]. The DNA fragment inserted contains the lacI gene as well as the lac UV5 promoter, eliminating the need to rely on the host cell's lac repressor to keep the promoter substantially shut off in the multicopy plasmid. This fragment was obtained from plasmid pMCl [Calos, *Nature London*, 274:762–765 (1978)]. The 1724 base-pair fragment contains the lacI gene, the lac UV5 promoter region, and the beginning of the lacZ gene isolated from pMCl by partial digestion with HincII and cloned into the BamHI site of pBR322 using synthetic linkers. The BamHI fragment isolated from this clone was then ligated into the BglII site of pAR1173 ahead of gene 1, taking advantage of the identity of the 4-base extensions produced by BglII and BamHI. A resulting plasmid in which the lac UV5 promoter is directed toward gene 1 is pAR1219. When induced with IPTG, this plasmid produces large amounts of active T7 RNA polymerase.

Figure 1:
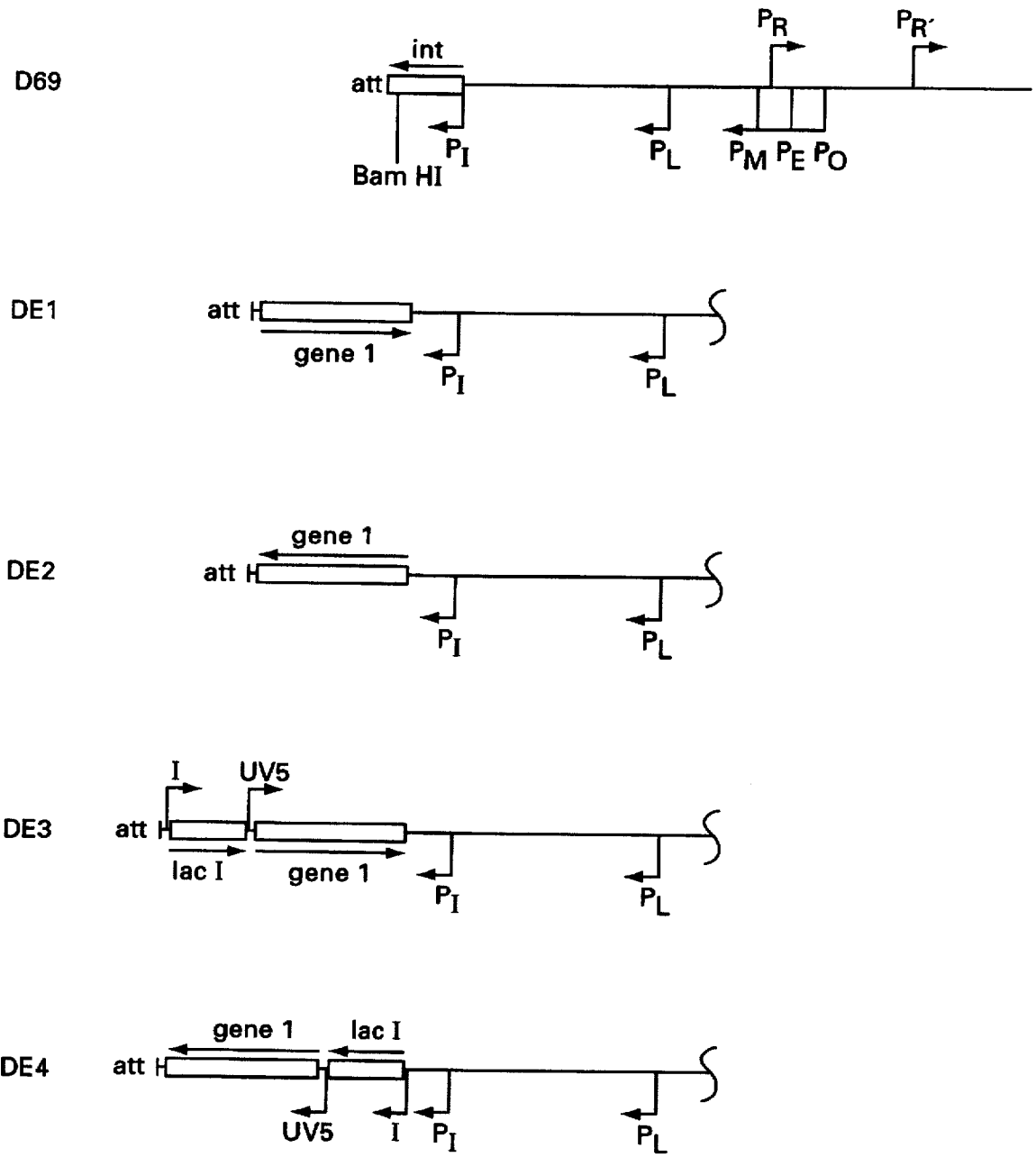
FIG. 1. Locations and orientations of E. coli promoters and inserted genes in D69, DE1, DE2, DE3 and DE4. These phages are also described in Table 1. The DNA between the attachment site (att) and the right end of the mature phage DNA is represented (for a map of the entire lambda DNA molecule see phage 473 of Hendrix et al., Lambda II, Cold Spring Harbor Laboratory Press, Cold Spring Harbor, N.Y. 1983). The locations of known E. coli promoters and the BamHI cloning site within the int gene of D69, and the locations and orientations of the lacI promoter, the lacI Eerie, the lacUV5 promoter, and T7 gene 1 in the different derivatives of D69 are represented to scale.

The active gene for T7 RNA polymerase, alone (pAR1151) or under control of the lac UV5 promoter (pAR1219), was placed in the BamHI site of the lambda cloning vector D69 [described in Mizusawa, et al., cited above]. The locations and orientations of *E. coli* promoters and inserted genes in D69, DE1, DE2, DE3, and DE4 are shown in FIG. 1, and the phages are described in Table 1. All the phages contain both a mutation that eliminates the BamHI site at nucleotide 5505 of lambda DNA, and a deletion of the DNA between the EcoRI sites at nucleotides 21,226 and 26,104. The cloning site in D69 is the BamHI site at nucleotide 27,972 in the int gene. The orientation in which mRNA for T7 RNA polymerase would be transcribed from the PL and PI promoters of the phage is designated E, for expressed (in Table 1); the opposite orientation is designated S, for silent. The immunity region between nucleotides 34,379 and 38,617 either has been replaced by the immunity region of phage 21 or is the lambda immunity region having the cI857 and ind1 mutations. The nin5 deletion (Δ) removes nucleotides 40,502, to 43,307. In the orientation represented by DE1, no *E. coli* promoters that would direct transcription of gene 1 mRNA are known to be present in D69 DNA; DE3 contains gene 1 in the same orientation but under control of the lacUV5 promoter. In the opposite orientation, represented by DE2, the PL and PI promoters of D69 can direct transcription of gene 1 mRNA; DE4 contains gene 1 in this orientation but is also under control of the lac UV5 promoter. All four of these strains grow well and produce high-titer lysates, and all have been obtained as lysogens of HMS174 and BL21. Apparently, the presence of the T7 RNA polymerase gene, whether expressed or not, has little effect on lambda growth or lysogeny in the usual hosts.

Addional derivatives carrying gene 1 were obtained by crossing DE2 (in which gene 1 is under control of PL and PI) with lambda cI857ind1Sam7. The cI857 mutation would make expression from the PL promoter temperature-inducible, and the Sam7 mutation would prevent lysis of the infected or induced cells. Three recombinants selected for further use all appear to have retained the left arm of DE2 and to have lost the nin5 deletion; DE6 retains imm[21] and has acquired the Sam7 mutation; CE2 has acquired imm[λ] (cI857ind1); and CE6 has acquired both imm[λ] (cI857ind1) and Sam7.

TABLE 1

Derivatives of the Lambda Cloning Vector D69 that Carry T7 Gene 1

| Phage | Fragment cloned into int | Orientation | Immunity | nin5 | Sam7 |
|---|---|---|---|---|---|
| D69 | None | | 21 | Δ | + |
| DE1 | T7 gene 1 | S | 21 | Δ | + |
| DE2 | T7 gene 1 | E | 21 | Δ | + |
| DE3 | lacUV5-gene 1 | S | 21 | Δ | + |
| DE4 | lacUV5-gene 1 | E | 21 | Δ | + |
| DE6 | T7 gene 1 | E | 21 | + | am |
| CE2 | T7 gene 1 | E | λcI857 | + | + |
| CE6 | T7 gene 1 | E | λcI857 | + | am |

D69 is described by Mizusawa & Ward (1982). All phages in the Table contain both a mutation that eliminates the BamHI site at nucleotide 5505 of lambda DNA and a deletion of the DNA between the EcoRI sites at nucleotides 21,226 and 26,104. The cloning site in D69 is in the BamHI site at nucleotide 27,972 in the int gene. The orientation in which mRNA for T7 RNA polymerase would be transcribed from the $p_L$ and $p_I$ promoters of the phage (see FIG. 1) is designated E (for expressed); the opposite orientation is designated S (for silent). The immunity region between nucleotides 34,379 and 38,617 either has been replaced by the immunity region of phage 21 or is the lambda immunity region having the cI857 and ind1 mutations. The nin5 deletion (Δ) removes nucleotides 40,502 to 43,307.

EXAMPLE 5

Induction of T7 RNA Polymerase from pAR1219

When cultures of HMS174/pAR1219 or BL21/pAR1219 were induced with IPTG, T7 RNA polymerase was produced at a rapid rate and accumulated to levels such that it was the major protein of the cell. Enzyme activity, as assayed in crude extracts, increased along with accumulation of the protein. The rate of increase of turbidity of the culture was almost as high for the induced culture as for a parallel uninduced culture, and colonies could form on plates containing inducer. This suggests that T7 RNA polymerase itself is not very toxic to the cells.

EXAMPLE 6

Purification of T7 RNA Polymerase from BL21/pAR1219

T7 RNA polymerase was isolated from induced cultures of BL21/pAR1219 growing in a shaking flask at 37° C. in a relatively rich medium [tryptone broth plus M9, Studier, *Virology*, 39, 562–574 (1969)]. IPTG was added to a final concentration of 0.4 mM when the cells reached a few times $10^8$ per ml and shaking at 37° C. was continued another 4 hrs. These cells contain perhaps 10–20% of the total protein as T7 RNA polymerase, virtually all of it soluble and active.

T7 RNA polymerase can be purified from the induced cells by conventional techniques, for example, Chamberlin, et al., *Nature*, 228, 227–231 (1970), and typically about 10–15 mg of essentially pure protein can be obtained from 100 ml of culture (about 1 g of packed cells). BL21 was used as the host cell because we have found it to lack a protease found in HMS174 (and in many laboratory strains of *E. coli*) that can nick the T7 RNA polymerase protein during purification. However, essentially intact T7 RNA polymerase can be purified from protease-containing strains if the protease is removed at an early stage of the purification.

The purified enzyme is very active and specific in transcribing DNA that has a promoter for T7 RNA polymerase, as demonstrated by electrophoretic analysis of the DNA template and the RNAs produced from it. Almost all of the RNA produced when purified enzyme was used to transcribe a mixture of two DNA fragments, one of which contained a promoter for T7 RNA polymerase and the other of which did not, was of the size expected if it had started at the promoter and ended at the end of the fragment. This indicates that the transcription was specific and the enzyme was free of RNase activity. At a high enzyme concentration all of the precursors were incorporated into RNA in 15 minutes; at a lower enzyme concentration, incorporation continued for at least an hour. In both cases, the DNA fragments remained intact, indicating that the enzyme was free of DNase activity.

EXAMPLE 7

T7 RNA Polymerase Provided B, Infection

Each of the D69 derivatives listed in Table 1, except DE1, produces enough T7 RNA polymerase during infection to generate high-level expression of target genes cloned in a plasmid under control of a T7 promoter. The following procedure, using CE6 as the phage, produces efficient infection and high-level expression of the target gene protein.

Cultures are grown at 37° C., usually in a shaking incubator or waterbath, and plasmid-containing cells are grown in the presence of ampicillin, usually at 20 µg/ml. In order to obtain efficient infection (as measured by loss of colony-forming units), cultures are grown in the presence of maltose (and no glucose) to induce the lambda receptor. When the multiplicity of infection is higher than about 20 infectious phage particles per cell, the overall rate of protein synthesis after infection is drastically reduced and little protein is produced from the target gene. Protein synthesis was completely abolished in five different cultures after infection by 56 phage particles per cell, and almost completely abolished in three of them after infection by 28 particles per cell. All of the cultures retained active protein syntehsis at multiplicities of 7 and 14, and achieved high rates of synthesis of proteins whose genes are transcribed by T7 RNA polymerase. Inhibition of protein synthesis at high multiplicities is complete within five minutes after adding the phage. Because of this effect, optimal expression of target genes is achieved at multiplicities of 5 to 10—high enough to infect almost every cell, but low enough that protein synthesis is not inhibited.

Figure 2:
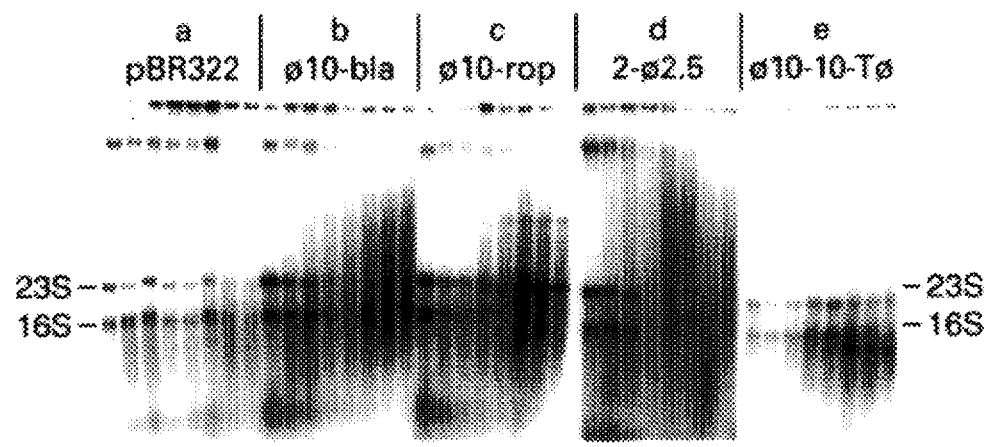
FIG. 2. Time-course of RNA synthesis after infection of different plasmid-carrying cultures by CE6. Cultures of HMS174 carrying different plasmids were grown in modified B2 medium containing 20 µg ampicillin/ml and infected with approximately 7 infectious particles of CE6/cell, as described in example 7. Samples of culture were labeled for 5 min with $^{32}PO_4$ (25 µCi/ml), and the cells were collected by centrifugation and suspended in an equal volume of 10 mM-sodium phosphate (pH 7.0), 2 mH-Na$_3$EDTA, 1% (w/v) sodium dodecyl sulfate, 1% (v/v) β-mercaptoethanol, 10% (v/v) glycerol, 0.01% (w/v) bromophenol blue. Each sample was mixed with 1/9 vol. 37% (v/v) formaldehyde, placed in a boiling waterbath for 2 min, and then an amount equivalent to 5 µl of culture was subjected to electrophoresis in a 1% (w/v) agarose gel containing 50 mM-sodium phosphate (pH 7.0), 2 mM-Na$_3$EDTA, 0.1% sodium dodecyl sulfate, followed by autoradiography. From left to right in each set, lanes represent samples labeled beginning 5 min before, and 0, 5, 10, 15, 30, 45 and 60 min after infection. The plasmids were: (a) pBR322, (b) pAR951, (c) pAR1494, (d) pAR219 and (e) pAR436. Where the plasmid contains any T7 promoters, T7 genes or Tφ, the order of these is indicated above the lanes, Whenever T7 genes are present, transcription from the T7 promoter is directed counterclockwise, which also directs transcription of the bla gene of the plasmid. When no T7 gene is present, the plasmid mRNA that would be transcribed from φ10 is indicated, bla for counterclockwise transcription and rop for clockwise. The positions of 23 S and 16 S ribosomal RNAs are indicated.

If cells are grown in M9 maltose, rates of protein synthesis can be measured by pulse-labeling with [$^{35}$S] methionine (FIG. 5), and if grown in B2 maltose, rates of RNA synthesis can be measured by pulse-labeling with $^{32}$PO$_4$ (FIG. 2). When the absorbance at 500 nm ($A_{600}$) of an actively growing culture reaches 0.3, glucose is added to give a concentration of 4 mg/ml, and the culture is grown for an additional 1 to 2 hours, during which the $A_{600}$ reaches 0.6 to 1, and the cell concentration is typically $5 \times 10^8$/ml. At this point, MgSO$_4$ is added to a final concentration of 10 mM, and purified CE6 phage is added to a final concentration of $2 \times 10^9$/ml (0.001 volume of a stock having an $A_{260}$ of 6). The multiplicity of infection is typically around 7, and the efficiency of infection is typically greater than 95%, as measured by loss of colony-forming ability. Addition of glucose and 10 mM MgSO$_4$ to the medium is not necessary, but seems to give slightly better production of protein from the target genes. Cells are usually harvested 3 hours after infection, enough time for substantial accumulation of target protein, but not enough time for uninfected cells to overgrow the culture.

EXAMPLE 8

T7 RNA Polymerase Provided by Induction of a Chromosomal Copy of the Gene

The lysogen BL21 (DE3) contains a single copy of the gene for T7 RNA polymerase in the chromosome, under the control of the inducible lacUV5 promoter. Some T7 RNA polymerase is produced from the prophage even in the absence of added inducer, so plasmids containing toxic target genes can be difficult or impossible to maintain in BL21(DE3). However, when the plasmid can be maintained, addition of isopropyl-β-D-thiogalactopyranoside (IPTG) induces the lacUV5 promoter to produce T7 RNA polymerase, which in turn initiates high-level expression of the target gene in the plasmid. The level of expression is usually comparable with that found in Example 7 (by infection).

Because toxicity of the target gene can lead to loss of the plasmid or the accumulation of non-functional mutants, cultures are sampled just before induction and titered for viable cells on plates without additives, or in the presence of 0.5 mg of ampicillin, 2.5 mol of IPTG, or both, added to the top agar. BL21(DE3) carrying a plasmid without a T7 promoter will form colonies on each of these plates, as will non-functional mutants that retain plasmid. In a typical culture useful for producing target proteins, almost all cells will form colonies on plates without additives or containing only amicillin. Less than 2% of the cells will form a colony on plates containing only IPTG, and less than 0.01% will form a colony on plates containing both ampicillin and IPTG.

Cultures have been grown in M9, M9ZB, ZY medium, or ZY medium supplemented with 0.4% (w/v) glucose. Induction is with 0.4 mM IPTG, when the culture reaches an $A_{600}$ of 1 (corresponding to about $5 \times 10^8$ to $10^9$ viable cells per ml). Cells are typically harvested 3 hours after induction, after substantial accumulation of target protein is achieved, but before the culture can be overgrown with unproductive cells or cells that have lost their plasmid.

EXAMPLE 9

Plasmids Used for Working Out the Properties of the T7 Expression System

Plasmids used to establish the utility of T7 RNA polymerase for directing the transcription and translation of cloned DNA in *E. coli* are listed in Table 2.

TABLE 2

| Plasmids | Genetic elements inserted |
| --- | --- |
| pBR322 | |
| pAR951 | φ10 |
| pAR1494 | φ10 (clockwise) |
| pAR946 | φ10-R0.3-0.3 |
| pAR219 | 2-φ2.5 |
| pAR511 | φ2.5-2.5 |
| pAR1012 | R4.7-φ4.7-4.7-5 |
| pAR525 | 6-6.3-φ6.5-R6.5-6.5 |
| pAR213 | 8-φ9-(9) (243aa) |
| pAR441 | φ9-9-φ10 |
| pAR436 | φ10-10-Tφ |

All inserts are in the BamHI site of pBR322 and all, except in pAR1494, are oriented so that transcription from T7 promoters proceeds counterclockwise in the conventional representation of pBR322. The order of T7 genetic elements in the inserted fragments is given, including T7 promoters (φ2.5, φ4.7, φ6.5, φ9 or φ10), intact T7 genes (0.3, 2, 2.5, 4.7, 5, 6, 6.3, 6.5, 8, 9 or 10), RNase III cleavage sites (R0.3, R4.7, R6.5), and the Tφ transcription terminator. The sizes and functions of proteins specified by the plasmids are given in Table 3. Plasmid pAR213 carries all of gene 8 and a large fragment of gene 9, predicted to direct a T7-pBR322 fusion protein that is 243 amino acid residues (aa) long.

TABLE 3

Sizes and Functions of Proteins Specified by Plasmids

| Gene | No. of amino acids | $M_r$ | Function |
| --- | --- | --- | --- |
| A. For pBR322 proteins | | | |
| bla precursor | 285 | 31,393 | |
| bla processed | 263 | 28,899 | Beta-lactamase |
| rop | 63 | 7226 | Control of replication |
| B. For T7 proteins | | | |
| 0.3 | 116 | 13,678 | Anti-restriction |
| 2 | 63 | 7043 | Anti-E. coli RNA polymerase |
| 2.5 | 231 | 25,562 | DNA-binding |
| 4.7 | 135 | 15,208 | Unknown |
| 5 | 704 | 79,692 | DNA polymerase |
| 6 | 347 | 39,995 | Exonuclease |
| 6.3 | 37 | 4088 | Unknown |
| 6.5 | 84 | 9474 | Unknown |
| 8 | 535 | 58,989 | Head-tail junction |
| 9 | 306 | 33,766 | Head assembly |
| 10A | 344 | 36,414 | Major head protein |
| 10B | 397 | 41,800 | Minor head protein |

It is assumed that the bla precursor does not retain the initial methionine residue but that the rop protein does. The gene 10B protein of T7 is produced by frameshifting during translation of the 10A mRNA. The relative mobilities of T7 proteins in gel electrophoresis in the presence of sodium dodecyl sulfate do not always correspond to their relative molecular weights.

EXAMPLE 10

Production of RNA in *E. coli*

Figure 3:
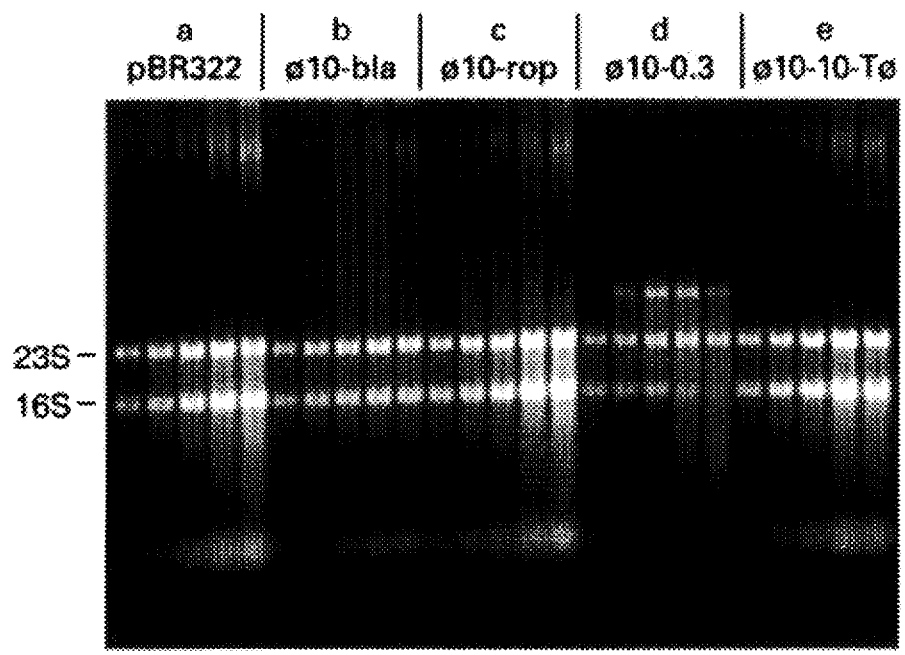
FIG. 3. Accumulation of RNA produced by T7 RNA polymerase. Cultures of BL21(DE3) carrying different plasmids were grown in M9ZB medium containing 20 µg ampicillin/ml, and synthesis of T7 RNA polymerase was induced by adding 0.4 mM-IPTG. The titer of a sample of culture removed before IPTG was added showed that almost all cells in each culture contained plasmid. Cells were collected by centrifugation, resuspended in 1.5 vol. 50 mM-Tris-HCl (pH 6–8), 2 mM-Na$_3$EDTA, 1% sodium dodecyl sulfate, 1% β-mercaptoethanol, 10% glycerol, 0.025% bromophenol blue, heated for 2 min in a boiling waterbath, and an amount equivalent to 3.3 µl of culture was subjected to electrophoresis in a 1.4% agarose gel in 40 mM-Tris-acetate (pH 8.0), 2 mM-Na$_3$EDTA. RNA was visualized by ethidium bromide fluorescence. From left to right in each set, lanes represent samples collected immediately before, and 0.5, 1, 2 and 3 h after IPTG was added to the culture. The plasmids were: (a) pBR322, (b) pAR951, (c) pAR1494, (d) pAR946 and (e) pAR436. Genes under control of T7 promoters in the plasmid are indicated above each set, as described in the legend to FIG. 2. Plasmid pAR946 (set (d)) also contains the R0.3 RNase-III cleavage site. The positions of 23 S and 16 S ribosomal RNAs are indicated.
Figure 4:
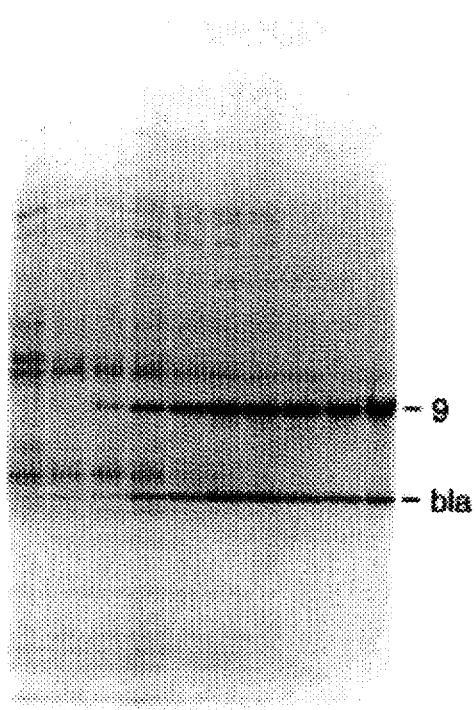
FIG. 4. Time-course of protein synthesis after infection of HMS174/pAR441 by CE6. A growing culture of HMS174/pAR441 was infected with approximately 14 infectious particles of CE6/cell, samples were labeled for 5 min with [$^{35}$S]methionine, and the labeled proteins were analyzed by gel electrophoresis followed by autoradiography. More than 99% of the cells in the culture were infected within 6 min, as indicated by loss of ability to form colonies. From left to right in the Figure, lanes represent samples that were labeled beginning at infection, and 5, 10, 15, 20, 30, 45, 60, 90 and 120 in after infection. The positions of the gene 9 and bla proteins are indicated.

T7 RNA polymerase can direct very high level synthesis of RNA, using T7 promoters in plasmids in *E. coli*. Rates of synthesis and levels of accumulation can be comparable to those for ribosomal RNAs (FIGS. 2 and 3). Transcription from the T7 promoter can also interfere with RNA synthesis by *E. coli* RNA polymerase (FIGS. 2b and 2c). If no transcription termination signals for T7 RNA polymerase are in the plasmid, transcription can continue around the entire plasmid to produce heterogeneous RNAs larger than plasmid length (FIGS. 2b, 2c and 2d, and FIGS. 3b and 3c). Where the RNA contains a single efficient RNase III cleavage site, the large heterogeneous RNAs are cut at this site and accumulate as a discrete band of the length expected for transcription once around the plasmid (FIG. 3d). Within an hour after induction, the amount of RNA accumulated in this band can approach that found in the ribosomal RNA bands (FIG. 3d). Where the plasmid DNA contains the transcription termination signal Tφ, transcription terminates efficiently to produce RNA of the expected length (FIGS. 2e and 3e). The RNAs appear to be relatively stable, and it seems likely that enough RNA accumulates to saturate the translation apparatus of *E. coli*.

Once active T7 RNA polymerase is present in the cell, transcription by the host cell RNA polymerase can be selectively inhibited. In the case of *E. coli*, this can be done by adding inhibitors such as rifampicin, which inhibits *E. coli* RNA polymerase but not T7 RNA polymerase, or by producing an inhibitor such as the gene 2 protein of T7 (FIG. 3d), which binds to *E. coli* RNA polymerase and inactivates it. This can be useful in applications where it is desirable or necessary that the transcripts from the T7 promoter be the only ones being produced in the cell.

Example 11

Time Course and Rate of Target Protein Synthesis

T7 gene 9 protein is efficiently synthesized in *E. coli*, and plasmid pAR441 was used to analyze optimum conditions for protein synthesis directed by the T7 expression system. The –lactamase mRNA is also transcribed by T7 RNA polymerase in this plasmid. Upon CE6 infection of HMS174/pAR441, synthesis of gene 9 protein and β-lactamase begins to increase 10 to 15 minutes after infection, and by 15 to 20 minutes after infection these proteins are the most rapidly synthesized in the cell. Their rate of synthesis continues to increase until at least 30 minutes after infection and remains at a very high level for at least another 90 minutes. During this period, the rate of synthesis of host proteins gradually declines, and there is little evidence for synthesis of lambda proteins. Synthesis of T7 RNA polymerase can be detected, but remains at a relatively low level; apparently, large amounts of T7 RNA polymerase are not needed in order to direct most of the protein synthetic capacity of the cell to the production of target proteins. The rate of synthesis of gene 9 protein is considerably higher than that of β-lactamase, even though there is every indication that the two mRNAs are produced in comparable amounts and are comparably stable.

Example 12

Target Protein Synthesis under Different Conditions for Delivery of T7 RNA Polymerase Experiments similar to those shown in Example 11 have examined stimulation of synthesis of gene 9 protein and B-lactamase after infection of HMS174/pAR441 by D69, DE1, DE3, and DE4 (see FIG. 1 for the location of gene 1 relative to *E. coli* promoters in these phages). As expected, no stimulation of target protein synthesis is observed after infection by D69, which can not supply any T7 RNA polymerase; nor is any stimulation observed after infection by DE1, a result indicating that little if any transcription of gene 1 occurs during infection by DE1. Stimulation by DE2, on the other hand, is comparable to that by CE6, as is stimulation by DE3 or DE4 in the presence of IPTG. In the absence of inducer, DE3 stimulates some target protein synthesis, but not as much as in the presence of inducer; apparently, the infecting copies of the lacUV5 promoter are only partially repressed. Likewise, DE4 stimulates considerably less target protein synthesis in the absence of inducer than in its presence or than is stimulated by DE2 (which contains no lacUV5 promoter); apparently, repression of the lacUV5 promoter in DE4 blocks transcription initiated at PL and/or PI. Finally, when DE2 infects an immune host, target protein synthesis is delayed by a few minutes and may not reach quite as high a level as in a sensitive host, but very substantial production of target protein occurs none the less. In an immune host, PL should be repressed; perhaps more DNAs enter the cell than can be repressed by the cI protein present at the time of infection, or perhaps transcription from the PI promoter, which is known to function at a low level in an immune host, is sufficient to produce this response.

Transcription of the target plasmid by T7 RNA polymerase is so active that it interferes with expression of lambda proteins during infection. As a result, the lambda infection is aborted and the cells do not lyse. Therefore, use of inhibitors of *E. coli* RNA polymerase, or infecting an immune cell to prevent lambda gene expression, or use of lambda mutants that cannot lyse the cell, are generally not needed nor useful for enhancing or extending target gene expression.

Comparably high-levels of expression are obtained whether T7 RNA polymerase is delivered by a phage carrier or is induced from a chromosomal copy of the gene. Making a lysogen of DE3 is a convenient way to place a single copy of gene 1 into the chromosome under control of the lacUV5 promoter. Such lysogens are very stable because gene 1 is inserted into the int gene, whose produce is needed for excising the prophage from the chromosome. The basal level of T7 RNA polymerase in the uninduced single-copy lysogen is considerably lower than when the cell contains the multi-copy plasmids pAR1151 or pAR1219, as measured by ability to plate 4107, a deletion mutant of T7 that completely lacks gene 1. This low basal activity allows a wide variety of target genes under control of a T7 promoter to be tolerated in the cell. Target genes that are too toxic to be established in a DE3 lysogen can still be expressed by infection with a gene 1-carrying lambda derivative.

EXAMPLE 13

Production of different target proteins in *E. coli*

Figure 5:
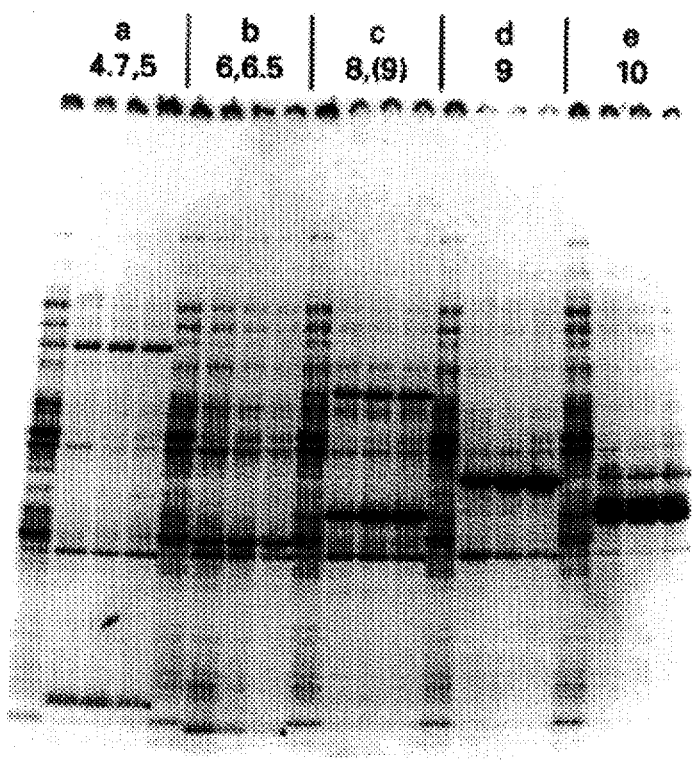
FIG. 5. Time-course of protein synthesis after infection of different plasmid-carrying cultures by CE6. Cultures of HMS174 carrying different plasmids were grown, infected with approximately 8 to 12 infectious particles of CE6/cell (except 25/cell for pAR1012), labeled for 5 min with [$^{35}$S]methionine, and the labeled proteins analyzed by gel electrophorosis followed by autoradiography. In each culture, more than 96% of the cells were infected within 6 min, as indicated by loss of ability to form colonies. From left to right in each set, lanes represent samples labeled immediately before, and 1, 2 and 3 h after infection. The plasmids were: (a) pAR1012, (b) pAR525, (c) pAR213, (d) pAR441 and (e) pAR436. The T7 proteins expressed under direction of T7 promoters in the plasmid are indicated above each set of lanes and marked by dots in the Figure; both the gene 10A and gene 10B proteins are marked. β-Lactamase is also expressed from T7 promoters in all of these plasmids, and its position is also marked in each set. The sizes of these proteins are given in Table 3, except for the fragment of gene 9 protein in set (c), which is predicted to contain 243 amino acid residues.

A variety of different T7 proteins having different degrees of toxicity to the host cell have been expressed in the T7 expression system, where T7 RNA polymerase has been delivered by infection with a lambda derivative or produced by induction from a chromosomal copy of gone 1. Protein patterns illustrating rates of target protein synthesis at different times after synthesis of T7 RNA polymerase was initiated are shown in FIG. 5, and patterns illustrating the accumulation of target proteins are shown in FIG. 6. Typically, the target proteins are produced at substantial rates, and synthesis of host proteins is greatly reduced. This shift in protein synthesis reflects the shift in mRNA population in favor of transcripts produced by T7 RNA polymerase, and the relatively high translational efficiency of the T7 mRNAs. High rates of synthesis of the target proteins can continue for at least three hours (as shown in FIG. 5) and have been observed to continue for at least seven hours in some of the cases we have examined. Target proteins can accumulate to become a substantial fraction of the total cell protein, perhaps 50% or more, within a few hours (FIG. 6). The relative rates of synthesis and accumulation of individual T7 proteins expressed in the T7 expression system differ considerably, and generally seem to parallel the relative rates of synthesis during T7 infection. It seems likely that the T7 expression system Produces saturating amounts of mRNA, and that the relative rates of protein synthesis reflect mainly the relative efficiencies of translation of the individual T7 mRNAs.

EXAMPLE 14

Vectors for Transcribing Target DNAs

T7 RNA polymer see is potentially capable of transcribing any DNA that is placed under control of a T7 promoter. Table 4 lists a set of plasmid vectors that contain a strong promoter for T7 RNA polymer see followed by one or more unique cloning sites. In pAR2529, the cloning site is followed by T$\phi$, the transcription terminator. These vectors are all derived from pBR322, and DNA from many sources can be cloned in them so that it can be transcribed by T7 RNA polymer see in vitro or in vivo. The DNA fragments containing the T7 promoter or T7 promoter and terminator have been designed so that they can easily be removed from certain of the vectors and used to create new expression sites in other plasmids, viruses, or chromosomes. The practitioner of the art will recognize that a wide range of different expression vectors could be created using these or similar DNA fragments that contain a T7 promoter or T7 promoter and terminator. Detailed description of some of the more useful vectors is disclosed in Rosenberg, et al. *Gene*, 56, 125–135 (1987) and follows.

TABLE 4

Vectors for transcribing cloned DNAs

| Vector | Isolation No. | Upstream site | Promoter | Cloning sites | Downstream Elements |
|---|---|---|---|---|---|
| | pAR1959 | BamHI | $\phi$10 | BamHI | |
| pET-1 | pAR2019 | | $\phi$10 | BamHI | |
| pET-2 | pAR2305 | BglII | $\phi$10 | BamHI | |
| pET-3 | pAR2529 | BglII | $\phi$10 | BamHI | T$\phi$ BglII |
| pET-5 | pAR2192 | | $\phi$10 | BamHI-EcoRI | Δ in pBR322 |
| pET-6 | pAR2369 | BamHI | $\phi$10 | StuI-BamHI | |
| pET-7 | pAR2463 | BglII | $\phi$10 | StuI-BamHI | |

Plasmid pAR1959 was constructed by inserting a TaqI-XbaI fragment of T7 DNA (nucleotides 22,880–22,928) containing the $\phi$10promoter for T7 RNA polymerase into the BamHI site of pBR322 by using the synthetic linker CGG-GATCCCG. The fragment extends from nucleotides −23 to +26 relative to the start of the RNA and is oriented so that transcription from the $\phi$10 promoter is directed counterclockwise, opposite to transcription from the tetracycline promoter. Counterclockwise transcription through this region by *E. coli* RNA polymerase is low enough to permit relatively toxic genes to be cloned under control of the T7 promoter. T7 RNA polymerase initiates active and selective transcription at the $\phi$10 promoter both in vivo and in vitro.

To increase the usefulness and versatility of plasmids containing this $\phi$10 promoter fragment, the following derivatives were constructed:

pAR2019, in which the upstream BamHI site of pAR1959 has been removed by opening, filling in, and re-ligating. This leaves the downstream BamHI site as a unique cloning site.

pAR2305, in which the upstream BamHI site of pAR1959 has been converted to a BglII site by opening, filling in, adding the linker GAGATCTC, cutting with BglII, and re-ligating. Both the upstream BglII site and the downstream BamHI site are unique in this plasmid. New $\phi$10 vectors can be created by moving the BglII-BamHI fragment to a unique BamHI site.

pAR2529, in which the transcription terminator for T7 RNA polymerase, T$\phi$, has been added just downstream of the BamHI cloning site of pAR2305. A fragment of T7 DNA containing T (nucleotides 24,106–24,228, where transcription terminates at nucleotide 24,209) was Joined to the BamHI cloning site of pAR2305 through the sequence [GGATCC]GG-T$\phi$-CCGGATCGAGATCTCGATCC, where the final C is nucleotide 375 in the BamHI site of pBRS22. The downstream linker contains a BglII site, so the entire $\phi$10-BamHI-T fragment can be removed from this plasmid as a BglII fragment for transfer to other vectors.

pAR2192, in which the DNA between the BamHI and EcoRI sites of pAR2019 (originally from pBR322) has been deleted to leave the BamHI and EcoRI sites in the sequence GGATCCGTTAAC. This deletion removes the tetracycline promoter, so transcription by E. coli RNA polymerase across these cloning sites should be relatively low in both directions. If a fragment cloned into the BamHI site has no EcoRI sites, cutting the plasmid at the EcoRI site will cause the RNA made by purified T7 RNA polymerase to end only a few nucleotides past the end of the cloned fragment.

In all of the above plasmids, the RNA transcribed from a cloned DNA will begin with 26 nucleotides of T7 sequence and a CG from the linker sequence before the first G of the BamHI cloning site. The first 21 nucleotides of the RNA could potentially fold into a relatively stable 8 base-pair stem-and-loop structure (FIG. 7).

In order to be able to make RNA with only two nucleotides preceding the transcript of a cloned DNA, we took advantage of the fact that nucleotides −1 to +2 of the φ10 promoter sequence are AGG, which is half of a StuI site (AGG'CCT). The cloned sequence downstream of +2 in pAR1959 and pAR2305 was replaced by the remaining half of the StuI site followed immediately by a BamHI site in the sequence CCTGGATCC to create pAR2369 and pAR2463 (FIG. 8). The StuI site is unique in these plasmids, and can be used to place any DNA fragment at position +3 by blunt-end ligation.

In spite of the replacement of nucleotides +3 to +6 of the conserved sequence of the φ10 promoter, T7 RNA polymerase initiates RNA chains efficiently at this promoter in both plasmids. We expect that most or all DNA fragments inserted at the StuI site will be transcribed by T7 RNA polymerase to produce RNAs having only an additional GG at their 5' end. Cutting at the downstream BamHI site can also be used to end transcription only a few nucleotides past the end of the cloned fragment.

The sequence CCTGG found in the StuI-BamHI sequence of pAR2369 and pAR2463 is a cleavage site for BstNI and also a methylation site for the dcm methylase of E. coli. Methylation at this site prevents cleavage by StuI, so plasmid must be prepared from a dcm⁻ strain if it is to be cut efficiently at the StuI site. BL21 is a B strain of E. coli and as such is dcm⁻.

EXAMPLE 15

Vectors for Transcribing and Translating DNAs in E. coli

Different mRNAs are translated with widely different efficiencies in E. coli. The factors affecting efficiency of translation are not completely understood, but coding sequences usually start with AUG, and the mRNA usually contains upstream sequences (the Shine-Dalgarno sequences) thought to be important in binding the mRNA to the ribosome and initiating translation. The structure of the mRNA is also thought to be important.

The major capsid protein of T7, specified by gene 10, is made very efficiently during T7 infection, much more rapidly than any host protein. The mRNA initiated at the φ10 promoter contains 63 nucleotides ahead of the gene 10 initiation codon (FIG. 9), and this leader sequence seems likely to be responsible at least in part for the efficiency of translation of the gene 10 mRNA. The mRNA begins with 21 nucleotides that could form a relatively stable stem-and-loop structure, and continues with an apparently unstructured, AT-rich region that contains a good Shine-Dalgarno sequence ahead of the initiation codon. The sequence containing the initiation codon forms part of an NdeI cleavage site in the DNA (CATATG). Specific cleavage of the DNA at this site can be used to fuse coding sequences directly to the initiation codon of gene 10. An NdeI cleavage site is particularly useful for this purpose because the initiation codon for any protein can potentially be made to be part of an NdeI cleavage site in its DNA by changing only upstream, noncoding nucleotides, and without changing any coding sequences for the protein. Fusing coding sequences to the leader sequence in such a way could place the initiation codon for any protein at a site known to be efficiently translated in E. coli.

We have constructed vectors containing the 10 promoter and gene 10 protein initiation region to a point just past the 11th codon for the gene 10 protein. Besides the NdeI cleavage site at the initiation codon, the sequence contains an NheI cleavage site at the second and third codons. In addition, we have placed BamHI cleavage sites after the 11th codon, using linker oligonucleotides of three different lengths. Such a set of three vectors makes it relatively easy to fuse any coding sequence after the 11th codon of the gene 10 protein so that it will be in the correct reading frame to be translated from the gene 10 initiation site. In one set of vectors, the BamHI cloning sites are followed by Tφ, the transcription terminator. The DNA fragments containing the control sequences have been designed so that they can easily be removed from certain of the vectors and used to create transcription-translation sites in other plasmids, viruses or chromosomes. The practitioner of the art will recognize that a wide range of different expression vectors could be created using these or similar DNA fragments that contain a T7 promoter and a translation initiation site, with or without a transcription terminator. Detailed description of some of the more useful vectors is disclosed in Rosenberg, et al. Gene, 56, 125–135 (1987) and follows.

TABLE 5

Vectors for Transcribing and Translating Cloned DNAs

| Vector | Isolation No. | Upstream site | Expression signals | Fusion cloning site | Open frame | Downstream |
|---|---|---|---|---|---|---|
|  | pAR2075 | BamHI | φ10-s10 | BamHI (8mer) | ATC |  |
|  | pAR2078 | BamHI | φ10-s10 | BamHI (10mer) | GAT |  |
|  | pAR2084 | BamHI | φ10-s10 | BamHI (12mer) | GGA |  |
| pET-1c | pAR2120 |  | φ10-s10 | BamHI (8mer) | ATC |  |
| pET-1b | pAR2093 |  | φ10-s10 | BamHI (10mer) | GAT |  |
| pET-1a | pAR2098 |  | φ10-s10 | BamHI (12mer) | GGA |  |
| pET-2c | pAR2156 | BglII | φ10-s10 | BamHI (8mer) | ATC |  |
| pET-2b | pAR2106 | BglII | φ10-s10 | BamHI (10mer) | GAT |  |
| pET-2a | pAR2113 | BglII | φ10-s10 | BamHI (12mer) | GGA |  |

TABLE 5-continued

Vectors for Transcribing and Translating Cloned DNAs

| Vector | Isolation No. | Upstream site | Expression signals | Fusion cloning site | Open frame | Downstream |
|---|---|---|---|---|---|---|
| pET-3c | pAR3038 | BglII | φ10-s10 | BamHI (8mer) | ATC | TφEcoRV |
| pET-3b | pAR3039 | BglII | φ10-s10 | BamHI (10mer) | GAT | TφEcoRV |
| pET-3a | pAR3040 | BglII | φ10-s10 | BamHI (12mer) | GGA | TφEcoRV |

The parental plasmid for this set of plasmids is pAR2067, which was derived from pBR322 by eliminating the NdeI site at nucleotide 2298 by opening it, filling in, and re-ligating the blunt ends.

A TaqI-RsaI fragment of T7 DNA (nucleotides 22,880–22,998) containing the φ10 promoter for T7 RNA polymerase, the translation initiation site for the gene 10 protein has been inserted into the BamHI site of pAR2067. (Gene 10 specifies the major capsid protein of T7.) The fragment extends from nucleotides −23 to +96 relative to the start of the RNA and is oriented in each plasmid so that transcription from the φ10 promoter is directed counterclockwise, opposite to transcription from the tetracycline promoter. Initially, the fragment was cloned with a BamHI linker CGGGATCCCG (10 mer) attached to the upstream end and one of three BamHI linkers, CGGATCCG (8 mer), CGGGATCCCG (10 mer), or CGCGGATCCGCG (12 mer), attached to the downstream end of the T7 DNA fragment. This produced a set of three plasmids such that inserting a DNA fragment having an open reading frame into the downstream BamHI site will produce an in-frame fusion to the first 11 amino acids of the gene 10 protein in one of the three plasmids. If insertion is by means of a BamHI-compatible sticky end (GATC), the open reading frame generated by the 8 mer linker will be ATC, that by the 10 mer GAT, and that by the 12 mer GGA.

To make this set of plasmids convenient to use, the upstream BamHI site was eliminated by opening, filling in, and re-lighting, or was converted to a BglII site by adding the linker GAGATCTC to the filled in site, cutting with BglII and ligating. This leaves the downstream BamHI site as a unique cloning site in these plasmids. New vectors can be created by moving the BglII-BamHI fragment into any unique BamHI site.

A further modification has been to add Tφ, the transcription terminator for T7 RNA polymerase, just downstream of the BamHI cloning site. A fragment of T7 DNA containing Tφ (nucleotides 24,106–24,228, where transcription terminates at nucleotide 24,209) was joined to the BamHI cloning site through the sequence [GGATCC]GG-To-CCGGATATCC, where the final C is nucleotide 375 in the BamHI site of pBR322. The downstream linking sequence contains an EcoRV site (GAT'ATC), so the entire [φ10-s10-Tφ] fragment can be removed from this plasmid as a BglII-EcoRV fragment for transfer to other vectors. (These plasmids also contain one other EcoRV site, at nucleotide 187 of pBR322.)

Each of the plasmids in this set contains a unique NdeI site (CA'TATG) that includes the initiating ATG for the gene 10 protein. Any coding sequence that also begins at an NdeI site can be joined to the upstream translation signals for the gene 10 protein, and such a fusion will specify only amino acids of the desired protein. Initiation codons that are not naturally part of an NdeI site could potentially be converted to such by directed mutagenesis.

The second and third codons for the gene 10 protein specify an NheI site (G'CTAGC), which can also be used to link coding sequences to the beginning of the gene 10 protein. (These plasmids also contain one other NheI site, at nucleotide 229 of pBR322.)

EXAMPLE 16

Expression of Various Target DNAs in Vectors for Transcribing or Translating Cloned DNAs The vectors described in examples 14 and 15 have been used for transcribing and translating many different DNAs in vitro and in *E. coli* cells. Full length poliovirus cDNA was cloned into the EcoRI site of vector plasmid pAR2192 in both orientations and transcribed by purified T7 RNA polymerase to produce full length infectious poliovirus RNA and full length complementary RNA; and the full length cDNA was cloned in the StuI site downstream of the T7 promoter of pAR2369 and transcribed to produce full length, infectious poliovirus RNA having only two additional nucleotides at the 5' end and no more than seven nucleotides past the poly(A) tract at the 3' end, as described in van der Werf, et al., *PNAS*, U.S.A. 83, 2330–2334 (1986). DNA specifying the 23S and 5S rRNAs of the rrnB ribosomal operon of *E. coli* was cloned between the XbaI and BamHI sites of plasmid pAR2156 in the correct orientation for synthesis of the rRNAs from the T7 promoter, and DNA specifying the entire rrnB operon except for the natural promoters was cloned in the BamHI site of plasmid pAR2192 in both orientations; complete transcripts were made of each of these cloned DNAs by purified T7 RNA polymerase, and the ribosomal RNAs were produced in vivo in BL21 (DE3) by T7 RNA polymerase induced by IPTG from chromosomal copy of the T7 RNA polymerase gene under control of the lacUV5 promoter, as described in Steen, et al., *EMBO J.*, 5, 1099–1103 (1986). A fragment of poliovirus cDNA coding for a protease involved in processing the poliovirus polyprotein was cloned between the BamHI and HindIII sites of plasmid pAR2106 to form an in-frame fusion after the 11th codon of the T7 gene 10 protein; active protease was produced in HMS174 when T7 RNA polymerase was delivered to the cell by infection with CE6, as described in Toyoda, et al., *Cell*, 45, 761–770 (1986). These are only a few examples of the many uses already made of the vectors described in examples 14 and 15 to direct transcription of DNA fragments by purified T7 RNA polymerase or to direct in vivo expression of DNA fragments by T7 RNA polymerase in BL21(DE3) (after induction) or in HMS174 (after infection by CE6).

We claim:

1. A method for controlling the expression of a target gene, comprising:
   a) introducing into an *E. coli* host cell containing a gene encoding an RNA polymerase from a T7 bacteriophage, a target gene operatively linked to a promoter recognizable by the RNA polymerase from the T7 bacteriophage; and
   b) maintaining the host cell under conditions appropriate for expression of the target gene by the RNA polymerase from the T7 bacteriophage.

* * * * *